(12) United States Patent
Nordholm et al.

(10) Patent No.: US 8,127,922 B2
(45) Date of Patent: Mar. 6, 2012

(54) CATHETER RECEPTACLE PROVIDED WITH AN ANTIMICROBIAL COMPOUND

(75) Inventors: Agneta Nordholm, Öjersjö (SE); Martin Nyman, Källered (SE); Daniel Holm, Öjersjö (SE)

(73) Assignee: Astra Tech AB, Molndal (SE)

( * ) Notice: Subject to any disclaimer, the term of this patent is extended or adjusted under 35 U.S.C. 154(b) by 55 days.

(21) Appl. No.: 12/285,431

(22) Filed: Oct. 3, 2008

(65) Prior Publication Data
US 2009/0101531 A1    Apr. 23, 2009

Related U.S. Application Data

(60) Provisional application No. 60/960,556, filed on Oct. 3, 2007.

(30) Foreign Application Priority Data

Oct. 3, 2007   (EP) ..................... 07117801

(51) Int. Cl.
*B65D 83/10* (2006.01)
*B65D 81/24* (2006.01)
*A61M 27/00* (2006.01)

(52) U.S. Cl. ........ 206/364; 206/210; 206/438; 604/172; 604/265; 604/544; 53/431

(58) Field of Classification Search .................. 206/205, 206/207, 210, 363–365, 438, 484, 484.2, 206/571; 53/428, 431; 424/422, 423; 514/568, 514/574; 604/265, 326, 347, 544
See application file for complete search history.

(56) References Cited

U.S. PATENT DOCUMENTS

| 5,779,687 A * | 7/1998 | Bell et al. ..................... 604/265 |
| 6,409,717 B1 * | 6/2002 | Israelsson et al. ............ 604/544 |
| 6,716,200 B2 | 4/2004 | Bracken et al. |
| 7,066,912 B2 * | 6/2006 | Nestenborg et al. .......... 604/171 |
| 2003/0139730 A1 * | 7/2003 | Bracken et al. ............... 604/544 |
| 2006/0240069 A1 * | 10/2006 | Utas et al. ..................... 424/423 |

FOREIGN PATENT DOCUMENTS

| WO | WO-97/26937 A1 | 7/1997 |
| WO | WO-98/11932 A1 | 3/1998 |
| WO | WO-98/19729 A1 | 5/1998 |
| WO | WO-00/09173 A1 | 2/2000 |
| WO | WO-00/47494 A1 | 8/2000 |
| WO | WO-01/43807 A1 | 6/2001 |

* cited by examiner

*Primary Examiner* — Luan K Bui
(74) *Attorney, Agent, or Firm* — Birch, Stewart, Kolasch & Birch, LLP

(57) ABSTRACT

A catheter assembly (110, 210) comprising a catheter (130, 230) and a receptacle (120, 220) is disclosed. The receptacle is arranged to accommodate at least part of said catheter and having at least one opening (123) for withdrawal of said catheter. Further, the receptacle is provided with an antimicrobial compound (301) at least in the vicinity of the opening and at least on the outer surface of the receptacle, said antimicrobial compound inhibiting microbes from being transferred to said catheter while being withdrawn through said at least one opening.

24 Claims, 3 Drawing Sheets

US 8,127,922 B2

CATHETER RECEPTACLE PROVIDED WITH AN ANTIMICROBIAL COMPOUND

This Nonprovisional application claims priority under 35 U.S.C. §119(e) on U.S. Provisional Application No. 60/960,556 filed on Oct. 3, 2007, and under 35 U.S.C. §119(a) on Patent Application No(s). 07117801.6 filed in Europe on Oct. 3, 2007, the entire contents of which are hereby incorporated by reference.

TECHNICAL FIELD OF THE INVENTION

The present invention relates to a catheter assembly comprising a catheter and a receptacle, the receptacle accommodating at least part of the catheter and having at least one opening for withdrawal of the catheter. The present invention also relates to a method for manufacturing of such a catheter assembly.

BACKGROUND ART

Catheters find their use in many different medical applications, such as urinary catheters for bladder drainage.

These urinary catheters are used in a variety of populations, including the elderly, stroke victims, spinal cord-injured patients, post-operative patients and those with obstructive uropathy. Despite adherence to sterile guidelines for the insertion and maintenance of urinary catheters, catheter-associated infections continues to pose a major problem. When medical devices such as a catheter is introduced into the human cavity, the normal human defense barrier may be penetrated, which can result in introduction of bacteria, fungi, vira, or tissue-like or multiple organized cells. Urinary tract infection (UTI), for instance, is a problem associated with the use of urinary catheters, including hydrophilic catheters with hydrophilic coatings for intermittent use. It is estimated that almost one-quarter of hospitalized spinal cord-injured patients develop symptomatic UTI during their hospital course. Gram-negative *bacilli* account for almost 60-70%, *enterococci* for about 25% and *Candida* species for about 10% of cases of UTI. It is well known that persons practicing intermittent urethral catheterization as a daily routine often have problems with symptomatic UTI.

In order to maintain the catheter in a clean and preferably sterile condition, each catheter is normally pre-packed in a receptacle by the manufacturer.

Additionally, in order to facilitate the use and to improve cleanliness of the catheter, the assemblies have in recent years developed to comprise a rupturable wetting fluid pouch or container as well, where wetting of the catheter may be performed without the use of externally supplied water, and without breaking the sealed condition of it until intended use of the catheter. Such assemblies are disclosed in for instance WO 97/26937, WO 01/43807 and WO 98/11932. Further, so called "ready-to-use" catheters have been proposed, where the catheter is arranged in the receptacle together with a wetting fluid in such a way that the catheter is maintained in a wetted, activated condition by said fluid. Such ready-to-use catheter assemblies are disclosed in for instance WO 00/47494 and WO 98/19729.

Further, in order to maintain sterility and cleanness of the catheter, the catheter may be coated with an antimicrobial compound for prevention of bacterial infection. US 2006/0240069, for instance, discloses a use of at least one salt of organic acid(s), and preferably a benzoate or a sorbate, as an antimicrobial agent. The compound described can also be incorporated in a wetting fluid, usable for providing low-friction surface character of a hydrophilic coating of a catheter by treatment with the wetting fluid, for making the hydrophilic coating antimicrobial when activated by the wetting fluid. Further, WO 00/09173 discloses a stabilized composition having antibacterial, antiviral and/or antifungal activity characterized in that it comprises a silver compound. Light stabilized silver composition can be introduced into catheters or similar medical devices.

However, although antimicrobial coating as well as the maintenance of the catheter in a sterile condition serve to inhibit bacterial growth and prevent bacterial infections, insertion of the catheter into the urethra continues to constitute a risk for introduction of bacteria into the human body. One of the causes for this is that bacteria may still be transferred to the catheter during withdrawal of the catheter from its receptacle. Specifically, the withdrawal from the receptacle pose a problem when the outer surface of the receptacle is prone to come into contact with the catheter as the catheter is withdrawn, thus enabling bacteria from the receptacle to come into contact with the catheter.

Therefore, there is still a need for improved means for inhibiting bacterial infections and similar diseases related to growth and transfer of microbes in the use of catheters.

SUMMARY OF THE INVENTION

It is therefore an object of the present invention to provide a catheter assembly of the type mentioned by way of introduction and a method for manufacturing the same, in which the above related drawbacks are eliminated wholly or at least partly.

According to a first aspect of the invention, a catheter assembly comprising a catheter and a receptacle is provided, the receptacle accommodating at least part of the catheter and having at least one opening for withdrawal of the catheter. The receptacle is provided with an antimicrobial compound at least in the vicinity of the one opening and at least on the outer surface of the receptacle, the antimicrobial compound inhibiting microbes from being transferred to the catheter while it is being withdrawn through the at least one opening.

The invention likewise concerns a method of manufacturing a catheter assembly of the kind defined above. Thus, according to a second aspect of the invention, there is provided a method of manufacturing a catheter assembly comprising a catheter and a receptacle, comprising the steps of:

accommodating at least part of the catheter in the receptacle, providing the receptacle with at least one opening for withdrawal of the catheter, and providing the receptacle with an antimicrobial compound at least in the vicinity of the one opening and at least on the outer surface of the receptacle, the antimicrobial compound inhibiting microbes from being transferred to the catheter while it is being withdrawn through the at least one opening.

Incorporating an antimicrobial compound in a polymer is known in the art, and for instance U.S. Pat. No. 6,716,200 discloses an antimicrobial urine collection system, in which the urine collection bag is made from a polymer comprising an antimicrobial agent. However, according to the teaching of this document, the antimicrobial compound is solely to be incorporated in a urine collection bag and the catheter itself, not the receptacle in which the catheter is accommodated, which is the case for the present invention. The purpose of adding the antimicrobial agent to the material also differs, as the described invention aims to prevent pathogens from migrating from a urine collection bag up through a catheter and into the urethra. The purpose of the present invention on the other hand, is to inhibit bacteria to be transferred from the receptacle to the catheter as the catheter is withdrawn through the receptacle opening or openings.

The term "opening" is in this application used to indicate any part of the receptacle which is intended to be brought from a closed disposition to an open disposition when the catheter is to be released and/or activated for use.

The transfer of microbes is avoided by adding to or incorporating in the receptacle, at least in the vicinity of the openings and at least on the outer surface of the receptacle, add an antimicrobial compound. The compound functions to inhibit growth of bacteria on the receptacle, for instance colonization on the surface. Consequently, the risk of contaminating the catheter as it comes into contact with the outer surface of the receptacle during withdrawal through the receptacle opening or openings is reduced, and consequently the risk of bacterial infections and similar diseases is alleviated.

A catheter in accordance with the present invention is particularly useful for urinary catheters, and especially for single-use urinary catheters intended for intermittent use. Consequently, the risk of being infected by UTI decreases for, for instance, patients practicing intermittent urethral catheterization as a daily routine.

Furthermore the catheter preferably has, on at least part of its surface, a hydrophilic surface layer providing low-friction surface character of the device by treatment with a wetting fluid.

It is known in the art that by applying a hydrophilic coating to the catheter, a low-friction effect is activated as wetting fluid comes into contact with the hydrophilic surface. Consequently, the coating facilitates insertion of the catheter into a human cavity, for instance the urethra.

Preferably, the catheter assembly further comprises a wetting fluid.

By allowing a wetting fluid forming part of the catheter assembly, no additional wetting fluid is needed for activation of the catheter, which entails many advantages. For example, activation of the catheter could easily be accomplished in places where it is normally difficult to find an appropriate wetting fluid for this specific use. Further, it could be ensured that only a sufficiently clean and sterile fluid is used, thereby decreasing the risk for unwanted contamination of the catheter. Still further, the wetting of the catheter may be accomplished in a simpler and more convenient manner.

A suitable wetting fluid could typically be sterile water or saline.

The amount of wetting fluid provided is preferably sufficient for filling the receptacle to a certain degree and to ensure that an adequate wetting of the catheter is maintained.

The wetting fluid may furthermore be arranged in wetting contact with the hydrophilic surface layer of the catheter in the receptacle, for preservation of the hydrophilic surface layer in a wetted state during accommodation in the receptacle and provision of a ready-to-use catheter assembly.

The catheter assembly may also present a storage state in which the wetting fluid is kept separated from the hydrophilic surface layer of the catheter, and an activation state in which the wetting fluid is brought into contact with the hydrophilic surface layer before an intended use of the catheter.

The catheter is thus according to the former embodiment activated already during production, and is then maintained in an activated ready-to-use condition, whereas the wetting fluid of the catheter assembly according to the latter embodiment, initially is kept separated from the hydrophilic surface layer of the catheter during storage of the assembly, and is brought into contact with the hydrophilic surface layer upon activation prior to use.

After the receptacle is opened, the receptacle could either be ripped off and then disposed of, or, according to one embodiment, be maintained connected to the catheter and used as a urine collection bag. Utilizing the receptacle as a container for receiving the drained urine from the bladder may contribute to less spillage, as the catheter maintains connected to the receptacle during, as well as after, the drainage.

At least part of the receptacle may form an elongate pocket of length sufficient to accommodate at least the insertable length of the catheter.

Additionally, at least one opening is preferably arranged on the elongate pocket.

Even more preferred is for the receptacle to have at least two openings positioned such that an intermediate part of the elongate pocket may be used as an insertion aid for guiding and holding the wetted catheter during insertion into the human cavity, for instance the urethra.

To facilitate the removal of the catheter form the receptacle and the insertion into, for instance, the urethra of a patient, at least one area of weakness is preferably arranged on the receptacle in the area of the elongate pocket, in which the catheter is placed. The area of weakness provides, through for instance tearing or twisting, an opening in the receptacle, and positioning of this opening on the elongate pocket serves to facilitate unpacking of the catheter before intended use.

Most preferably, two such areas of weakness are provided and separated in the lengthwise direction of the receptacle. The intermediate part of the elongate pocket may be used as an insertion aid for guiding and holding the wetted catheter when it is inserted into, for instance, the urethra. There is therefore no need to directly handle the catheter for insertion thereof into the human cavity, which is an advantage as the outer surface of the catheter will be slippery due to the wetting procedure and therefore difficult to grip and furthermore because the possibility of contamination of the catheter at this stage is avoided, whereby the cleanness and sterility of the catheter may be maintained.

The at least one opening is preferably a tear opening.

The term "tear opening" is, in the context of this application, to be understood in a broad sense, meaning an opening which is torn open by pulling parts of the receptacle material in essentially opposite directions. This type of openings are well known in the art, and are often advantageous for many different reasons. However, these openings provide a risk of contamination of the catheter, since the contact may come into contact with the non-sterile outer surface of the receptacle during withdrawal. However, the present invention is also applicable and useful for receptacles having other types of openings, such as peel-openings.

The receptacle preferably comprises opening means for facilitating opening of the receptacle in order to expose the catheter prior to use. The opening means could comprise one or several areas of weakness as discussed in the foregoing, and preferably tear lines connected to one or several gripping handles, for instance pulling tabs. Pulling tabs may be arranged on one or both sides of the area of weakness, in order to facilitate tearing open the receptacle.

Preferably the receptacle is formed of a flexible plastics material, for which the advantage of a bendable receptacle arises, contributing to the catheter assembly being easy to stow.

Arranging the antimicrobial compound as a coating on the outer surface of the receptacle material, or even incorporate therein, are preferred manners in which the antimicrobial compound is added to the receptacle for prevention of bacterial growth. The presence of the compound is, in order to inhibit transfer of microbes from the receptacle to the catheter as the catheter is being withdrawn from the receptacle through one or several openings, most critical in the vicinity of the openings.

The amount of the antimicrobial compound in the receptacle material may be in the range 0.1 to 20 phr (parts per hundred resin), and preferably in the range 0.5 to 7.5 phr, and most preferably about 4.5 phr.

The antimicrobial compound is preferably an organic acid metal salt, and may further comprise phosphoric acid esters and zinc metal.

Furthermore, the antimicrobial compound may comprise one or several of silver nitrate, silver acetate or silver lactate.

The above stated antimicrobial compounds and their concentrations in the receptacle material have proven to provide suitable antimicrobial effectiveness. Thus, by usage of a catheter assembly in accordance with the present invention comprising either of these compounds, within the given ranges, the transfer of microbes from the receptacle to the catheter as the catheter is being withdrawn from the receptacle, is avoided.

Other aspects, benefits and advantageous features of the invention will be apparent from the following description and claims.

BRIEF DESCRIPTION OF THE DRAWINGS

For exemplary purpose, the invention will in the following be described in more detail by means of the specific embodiments, and with reference to the accompanying drawings, which illustrate.

DETAILED DESCRIPTION OF PREFERRED EMBODIMENTS OF THE INVENTION

Figure 1:
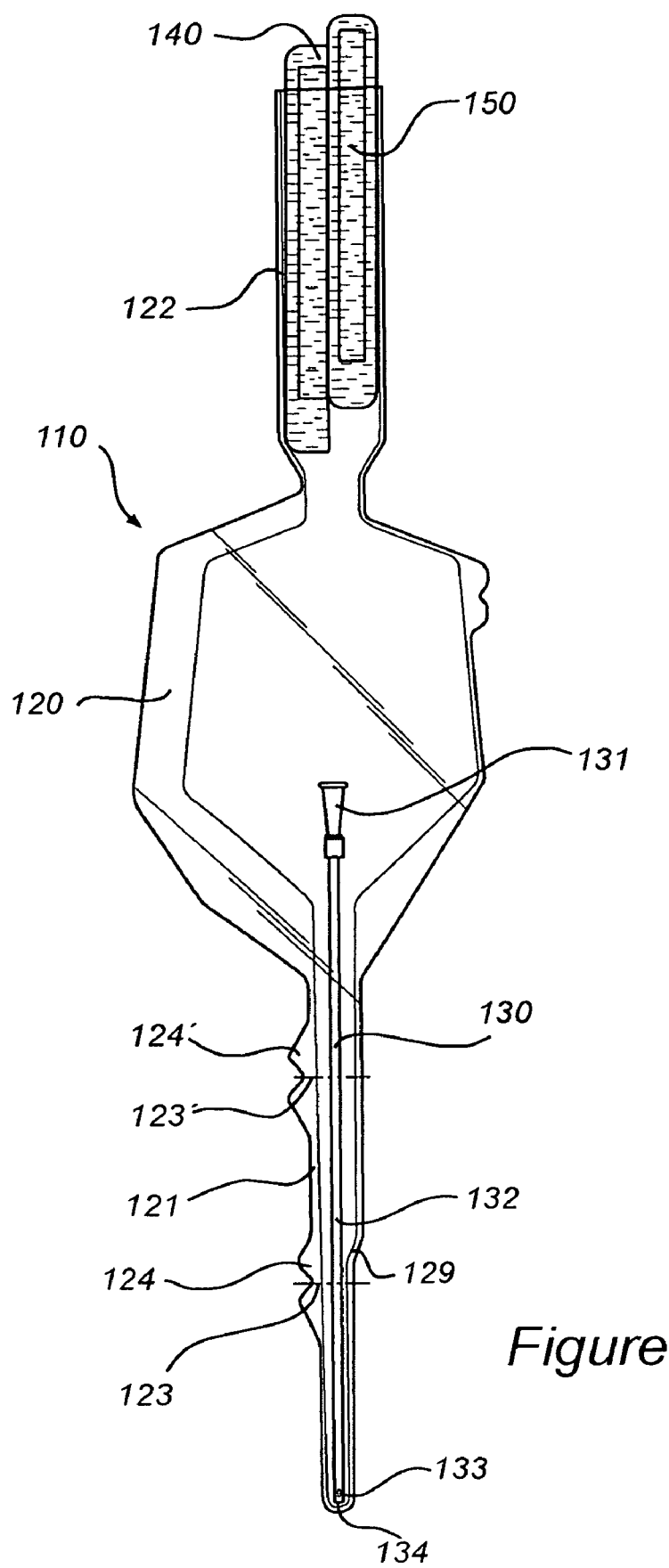
FIG. 1 shows a catheter according to a first embodiment of the present invention, with the receptacle forming a urine collection bag.

In the following detailed description, preferred embodiments of the present invention will be described. However, it is to be understood that features of the different embodiments are exchangeable between the embodiments and may be combined in different ways, unless anything else is specifically indicated. It may also be noted that, for the sake of clarity, the dimensions of certain components illustrated in the drawings may differ from the corresponding dimensions in real-life implementations of the invention, for instance the length of the catheter, the dimensions of the fluid compartments etc.

A catheter 130 as illustrated in FIG. 1, comprises a flared rearward portion 131 and an elongate shaft or tube 132 projecting forwardly from the rearward portion 131. An open-ended internal lumen (not shown) extends from the rear end of the rearward portion 131 to a drainage aperture 133 in a rounded tip 134 of the elongate tube 132. The rearward portion 131 may function as a connector of the catheter 130, being connectable to other devices, such as a urine collection bag, a drainage tube or the like.

At least a part of the elongate tube 132 forms an insertable length to be inserted through a body opening of the user, such as the urethra in case of a urinary catheter. By "insertable length" is normally, in the context of a hydrophilic catheter, meant the length of the elongate tube 132 which is coated with a hydrophilic material, for example PVP, and which is insertable into the urethra of the patient. Typically, this will be 80-140 mm for a female patient and 200-350 mm for a male patient.

According to the invention, and applicable for the embodiments disclosed herein, many different types of well-known hydrophilic materials can be used. For example, the catheter may be provided with a hydrophilic coating wherein the hydrophilic polymer coating comprises material selected from polyvinyl compounds, polysaccharides, polyurethanes, polyacrylates or copolymers of vinyl compounds and acrylates or anhydrides, especially polyethyleneoxide, polyvinylpyrrolidone, heparin, dextran, xanthan gum, polyvinyl alcohol, hydroxy propyl cellulose, methyl cellulose, copolymer of vinylpyrrolidone and hydroxy ethylmethyl acrylate or copolymer of polymethylvinyl ether and maleinic acid anyhydride. The preferred hydrophilic polymer is polyvinylpyrrolidone.

Upon use, the catheter 130 is wetted by a wetting fluid 150. The wetting fluid 150 serves the primary purpose of wetting the hydrophilic surface coating, whereby a low-friction character of the surface is produced and the catheter 130 becomes slippery and easy to insert into, for instance, the urethra of the patient. The wetting fluid 150 is preferably a water-based liquid, that is, using water as a solvent. Further, it is also possible to provide a dissolved antimicrobial compound in the fluid. Still further, the wetting fluid 150 could also comprise a dissolved hydrophilic polymer, and preferably the same type of hydrophilic polymer as in the hydrophilic coating of the catheter for which the wetting fluid 150 is intended. In this case, the amount of hydrophilic polymer in the wetting fluid is preferably in the range 0-20% of weight, and most preferably in the range 5-15%, and typically about 10%.

With reference to FIG. 1, a first embodiment of a catheter assembly 110 will now be described, the structure of which generally resembles embodiments previously disclosed in U.S. Pat. No. 6,409,717, said document hereby incorporated by reference.

The catheter assembly 110 comprises a wetting receptacle or bag 120, preferably of a transparent flexible plastics material. The receptacle 120 has an elongate pocket 121 at its forward end. At its rearward end 122 the receptacle presents an opening. The wetting receptacle 120 is adapted for accommodation of at least the insertable length of the catheter tube 132 in the elongate pocket 121.

The catheter assembly 110 further comprises a hydrophilic urinary catheter 130, of the type discussed in more detail in the foregoing.

The catheter 130 may be arranged in a package without any wetting fluid, wherein a wetting fluid is provided externally. However, preferably the catheter 130 is arranged in an assembly additionally comprising a wetting fluid 150, such as in the embodiment of FIG. 1. In this embodiment, the catheter assembly 110 comprises a wetting fluid 150 arranged in a separate compartment of the receptacle, and forming part of the assembly 110. More specifically, in the embodiment in FIG. 1, the catheter assembly 110 further comprises a wetting fluid container 140, in which the wetting fluid 150 is kept separated from the hydrophilic surface of the catheter 130 during storage.

The wetting fluid container 140 is openable, in order to enable activation of the catheter assembly 110. Thus, the activation is performed by opening the container 140 and releasing the wetting fluid 150 into the wetting receptacle 120 so that it comes into contact with the hydrophilic coating of the catheter. The wetting fluid container 140 may be openable by means of pressing, tearing, piercing, twisting, etc, which is per se well known in the art.

The wetting receptacle 120 preferably forms a sealed compartment around the catheter 130 and at least part of the wetting fluid container 140.

Furthermore, the wetting receptacle 120 preferably comprises opening means for facilitating opening of the receptacle in order to expose the catheter 130 for use. The opening means may comprise a tear line 123 connected to a gripping handle 124, such as a pulling tab, forming a tear opening. Hereby, the user may pull the gripping handle 124 and, thereby, tearing open the side wall of the wetting receptacle 120. Additionally, or alternatively, a gripping handle may be arranged in the opposite end of the tear line 123. However, alternative opening means are also feasible, such as tear-lines arranged in different fashions and locations, peel-off joints, etc.

Most preferably, at least two openings 123, 123' are positioned such that an intermediate part of the elongate pocket 121 may be used as an insertion aid for guiding and holding the wetted catheter 130 during insertion into the human cavity, for instance the urethra. In the exemplifying embodiment in FIG. 1, an additional tear line 123' is provided on the elongate pocket, along with a gripping handle 124'. The areas of weakness 123, 123' should if the receptacle 120 also serves as a urinary collection bag, which is the case in FIG. 1, preferably be placed beneath the restriction 129.

In a method of wetting the catheter 130 according to the embodiment in FIG. 1, the user first activates the catheter 130 by opening the wetting fluid container 140 within the bounds of the wetting receptacle 120, thereby releasing the wetting fluid 150 from the container 140 into the wetting receptacle 120. After a sufficient wetting period, the wetting receptacle 120 is opened, in order to expose the catheter 130 for insertion into a patient.

In the embodiment in FIG. 1, the wetting receptacle 120 also serves as a urine collection bag. In this case, after wetting of the catheter 130 for the predetermined duration in the same manner as described above, the bag 120 is turned upside down and the forwardmost portion of the elongate pocket 121 is torn off. The elongate shaft 132 of the catheter is then maneuvered through the opening in the forward end of the elongate pocket 121 and pulled out until the flared rearward portion 131 forms a mechanical seal connection with the opening at a restriction 129 of the receptacle. Thereafter, the catheter 130 is inserted into the urethra of the patient. Thus, being opened, the receptacle 120 maintains connected to the catheter 120 for receiving the drained urine from the bladder. However, this is merely optional, and a package not serving as a urine collection bag is equally feasible. Such an embodiment is illustrated in FIG. 2, which resembles the structure of some embodiments discussed in US 2005/043715, said document hereby incorporated by reference.

Alternatively, the catheter assembly 110 may comprise a package only partly enclosing the catheter 130, as is also disclosed in US 2005/043715, said document hereby incorporated by reference. It is also possible to arrange the wetting fluid container 140 not in a separate compartment of the receptacle 120, but integrated with the compartment holding the catheter 130. Hereby, the catheter 130 is activated already during production, and is then maintained in an activated, ready-to-use condition. Thus, in this embodiment, the hydrophilic surface layer is preserved in a wetted state during accommodation in the receptacle 120 and a ready-to-use catheter 130 is provided. In order to preserve this wetted condition, the compartment formed by the receptacle 120 and the catheter 130 is preferably gas sealed, and further, the receptacle 120 is preferably gas impermeable. In use, the receptacle 120 is simply opened, and the catheter 130 could immediately be introduced into the patient. Such an assembly 110 is for instance disclosed in U.S. Pat. No. 6,848,574, said document hereby incorporated by reference.

Figure 2:
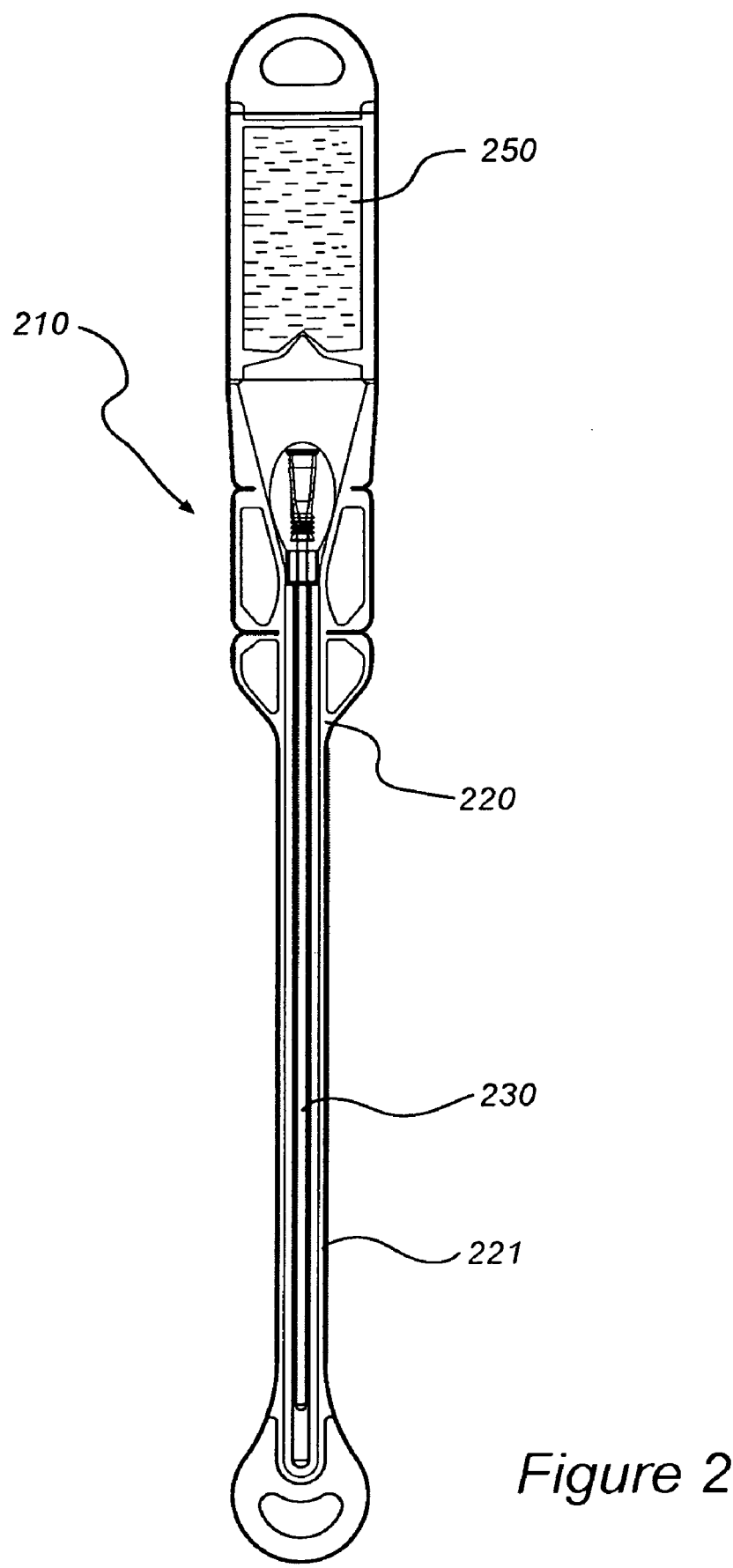
FIG. 2 shows a catheter assembly according to a second embodiment.

FIG. 2 shows a catheter assembly 210 which comprises a wetting receptacle or bag 220 and a catheter 230 comprising a flared rearward portion and an elongate shaft or tube projecting forwardly from the rearward portion 231. The receptacle 220 has an elongate pocket 221 at its forward end. Upon use, the catheter 230 is wetted by a wetting fluid 250.

In the embodiment of FIG. 2, the catheter is removed from the receptacle before or during insertion into the urethra, since the receptacle 220, as discussed in the foregoing, after opening should be disposed, that is, the receptacle 220 is in contrast to the catheter assembly 110 in FIG. 1 not serving as a urine collection bag. Other features, however, resemble features described in the foregoing in association to the embodiment in FIG. 1, why further description is omitted.

Figure 3A:
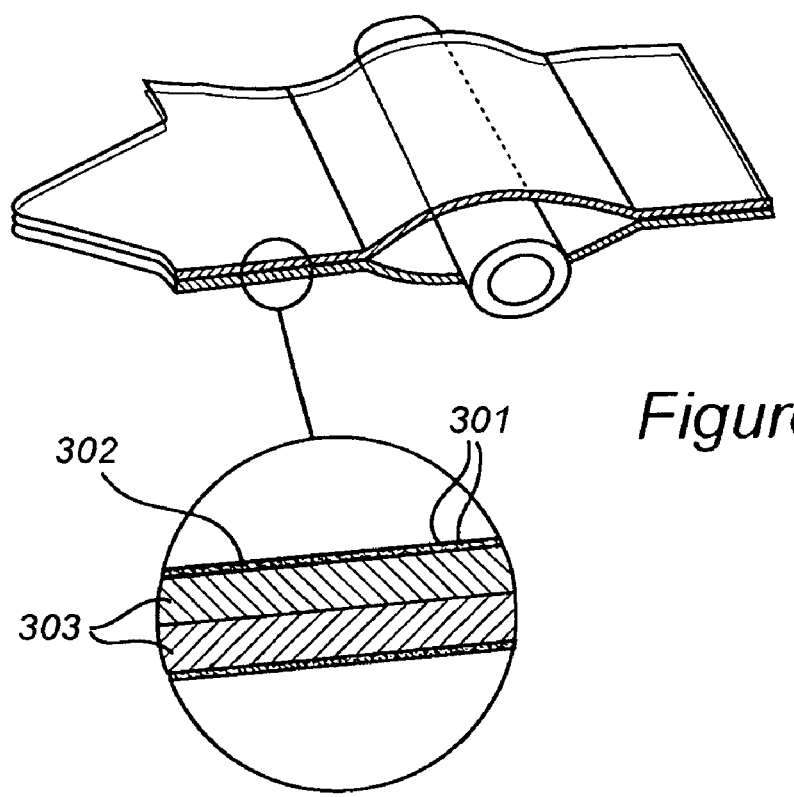
FIG. 3a shows a cross-section of the receptacle, wherein the antimicrobial compound constituting a layer on the outer surface of the receptacle material.
Figure 3B:
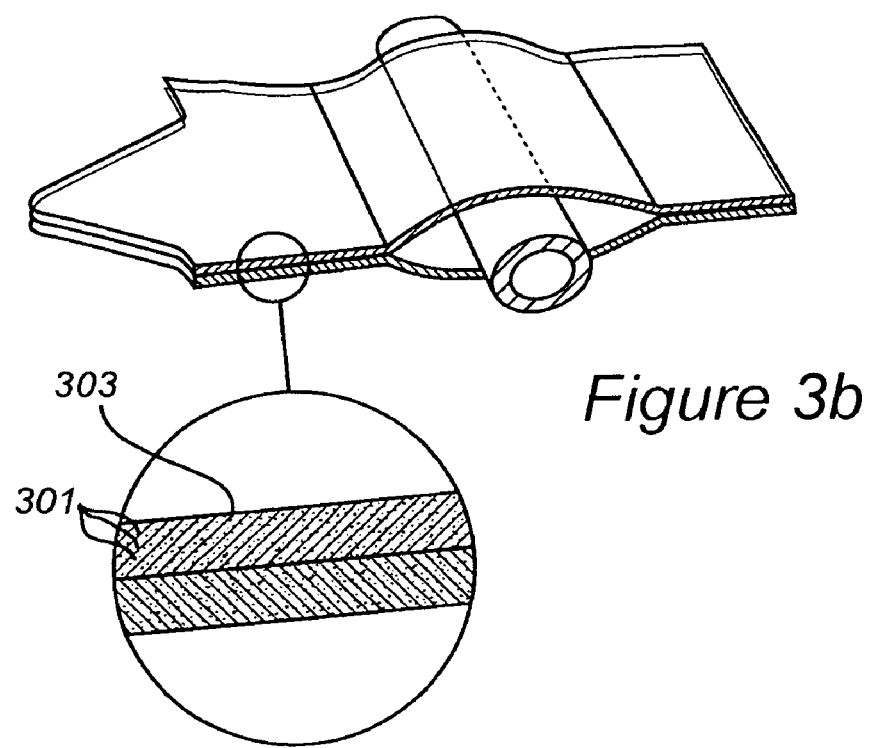
FIG. 3b shows a cross-section of the receptacle, wherein the antimicrobial compound incorporated in the receptacle material.

FIGS. 3a and 3b illustrate the antimicrobial compound 301 constituting a layer 302 on the outer surface of the receptacle material 303, and the antimicrobial compound 301 incorporated in the receptacle material 303, respectively.

Utilizing these exemplifying, preferred manners for providing the receptacle material 303 with the antimicrobial compound 301, enable the receptacle material 303 to inhibit bacterial growth. By adding the compound 301 particularly in the vicinity of the receptacle openings 123, 123', bacterial transfer from the receptacle 110, 210 to the catheter 120, 220, as the catheter 120, 220 is withdrawn from the receptacle 110, 210, is avoided.

The antimicrobial compound 301 in the receptacle material 303 could be in the range 0.1 to 20 phr (parts per hundred resin), and preferably in the range 0.5 to 7.5 phr, and most preferably about 4.5 phr.

Furthermore, the antimicrobial compound 301 is preferably an organic acid metal salt and comprises, according to one embodiment, phosphoric acid esters and zinc metal. According to another embodiment, the antimicrobial compound 301 is one of silver nitrate, silver acetate or silver lactate.

The invention has now been discussed in relation to different embodiments. However, it should be appreciated by those skilled in the art that several further alternatives are possible. For example, the features of the different embodiments discussed above may naturally be combined in many other ways.

It is further possible to use the invention for other types of catheters than urinary catheters, such as vascular catheters or the like.

Still further, it is possible to arrange the wetting fluid container in many different ways. For example, the container may be a separate container, but forming part of the assembly. Such a wetting fluid container may be arranged completely inside the receptacle, partly inside the receptacle, or completely outside the receptacle. Alternatively, the wetting fluid container may be an integrated compartment of the receptacle. This compartment may be separated from the compartment housing the insertable part of the catheter, or be integrated with such a compartment. In the latter case, the catheter may be maintained in a wetted, activated state.

Further, the wetting fluid container may be arranged close to the distal part of the catheter, close to the proximal part of the catheter, or in any other suitable location in the assembly. In case the wetting fluid is arranged separately from the insertable part of the catheter, the separation wall or joint could e.g. be a breakable or peelable membrane wall, but alternative embodiments are naturally feasible, such as various types of detachable or openable caps or closings. The wetting fluid container may be arranged to be discharged upon application of a twist, a compression, a pull or the like on the fluid container. Preferably the wetting fluid may be discharged without breaking or rupturing the receptacle, even though this may not be necessary, depending on the intended use, etc.

Many different materials could also be used for the different parts of the catheter assembly.

It will be appreciated by those skilled in the art that several such alternatives similar to those described above could be used without departing from the spirit of the invention, and all such modifications should be regarded as a part of the present invention, as defined in the appended claims.

The invention claimed is:

1. An intermittent and single use catheter assembly comprising a catheter and a receptacle, said receptacle forming a package for the catheter for maintenance of the catheter in a clean and sterile condition prior to use and accommodating at least part of said catheter and having at least one opening for withdrawal of said catheter,
wherein said package-forming receptacle is provided with an antimicrobial compound at least in the vicinity of said one opening and at least on the outer surface of the receptacle, said antimicrobial compound inhibiting microbes from being transferred to said catheter while being withdrawn through said at least one opening.

2. The catheter assembly according to claim 1, further comprising a wetting fluid.

3. The catheter assembly according to claim 1, wherein said catheter has on at least part of its surface a hydrophilic surface layer providing low-friction surface character of the device by treatment with a wetting fluid.

4. The catheter assembly according to claim 3, wherein said wetting fluid is arranged in wetting contact with said hydrophilic surface layer of said catheter in said package-forming receptacle, for preservation of said hydrophilic surface layer in a wetted state during accommodation in said receptacle and provision of a ready-to-use catheter assembly.

5. The catheter assembly according to claim 3, wherein said catheter assembly presents a storage state in which said wetting fluid is kept separated from said hydrophilic surface layer of said catheter, and an activation state in which said wetting fluid is brought into contact with said hydrophilic surface layer before an intended use of said catheter.

6. The catheter assembly according to claim 1, wherein said package-forming receptacle forms a urine collection bag.

7. The catheter assembly according to claim 1, wherein at least a part of said package-forming receptacle forms an elongate pocket of length sufficient to accommodate at least the insertable length of said catheter.

8. The catheter assembly according to claim 7, wherein said at least one opening is arranged on said elongate pocket.

9. The catheter assembly according to claim 8, wherein said package-forming receptacle has at least two openings positioned such that an intermediate part of said elongate pocket may be used as an insertion aid for guiding and holding the wetted catheter during insertion into the human cavity, for instance the urethra.

10. The catheter assembly according to claim 1, wherein said at least one opening is a tear opening.

11. The catheter assembly according to claim 1, wherein said package-forming receptacle is formed of a flexible plastics material.

12. The catheter assembly according to claim 1, wherein said antimicrobial compound constitutes a layer on the outer surface of said package-forming receptacle material.

13. The catheter assembly according to claim 1, wherein said antimicrobial compound is incorporated in said package-forming receptacle material.

14. The catheter assembly according to claim 13, wherein the amount of said antimicrobial compound in said package-forming receptacle material is in the range 0.1 to 20 phr (parts per hundred resin), and preferably in the range 0.5 to 7.5 phr, and most preferably about 4.5 phr.

15. The catheter assembly according to claim 1, wherein said antimicrobial compound is an organic acid metal salt.

16. The catheter assembly according to claim 15, wherein said organic acid metal salt comprises phosphoric acid esters and zinc metal.

17. The catheter assembly according to claim 1, wherein said antimicrobial compound is one of silver nitrate, silver acetate and silver lactate.

18. A method of manufacturing a an intermittent and single use catheter assembly comprising a catheter and a receptacle said receptacle forming a package for the catheter for maintenance of the catheter in a clean and sterile condition prior to use, comprising the steps of:
accommodating at least part of said catheter in said package-forming receptacle,
providing said package-forming receptacle with at least one opening for withdrawal of said catheter, and
providing said package-forming receptacle with an antimicrobial compound at least in the vicinity of said one opening and at least on the outer surface of the receptacle, said antimicrobial compound inhibiting microbes from being transferred to said catheter during withdrawal through said at least one opening.

19. The method according to claim 18, further comprising the step of:
providing said catheter, on at least part of its surface, with a hydrophilic surface layer providing low-friction surface character of the device by treatment with a wetting fluid.

20. The method according to claim 19, further comprising the step of:
arranging said wetting fluid in wetting contact with said hydrophilic surface layer of said catheter in said package-forming receptacle, for preservation of said hydrophilic surface layer in a wetted state during accommodation in said receptacle and provision of a ready-to-use catheter assembly.

21. The method according to claim 19, further comprising the step of:
arranging said catheter assembly such that it presents a storage state in which said wetting fluid is kept separated from said hydrophilic surface layer of said catheter, and an activation state in which said wetting fluid is brought into contact with said hydrophilic surface layer before an intended use of said catheter.

22. The method according to claim 18, wherein the step of accommodating at least part of said catheter in said package-forming receptacle, at least a part of said package-forming receptacle forms an elongate pocket of length sufficient to accommodate at least the insertable length of said catheter.

23. The method according to claim 22, wherein the step of providing said package-forming receptacle with said at least one opening for withdrawal of said catheter, said at least one opening is arranged on said elongate pocket.

24. The method according to claim 23, wherein said at least one opening comprises at least two openings positioned such that an intermediate part of said elongate pocket may be used as an insertion aid for guiding and holding the wetted catheter during insertion into the urethra.

* * * * *